(12) United States Patent
MacDonald et al.

(10) Patent No.: US 7,816,285 B2
(45) Date of Patent: Oct. 19, 2010

(54) PATTERNED APPLICATION OF ACTIVATED CARBON INK

(75) Inventors: John Gavin MacDonald, Decatur, GA (US); Roger Bradshaw Quincy, III, Cumming, GA (US); Jaeho Kim, Roswell, GA (US); Jeffrey Eldon Fish, Dacula, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 11/021,485

(22) Filed: Dec. 23, 2004

(65) Prior Publication Data
US 2006/0137568 A1    Jun. 29, 2006

(51) Int. Cl.
   *B32B 27/14* (2006.01)
   *A61F 13/15* (2006.01)
   *A61F 13/20* (2006.01)

(52) U.S. Cl. .......................... 442/69; 604/359

(58) Field of Classification Search ............... 604/359; 423/447.1, 447.5; 502/180
See application file for complete search history.

(56) References Cited

U.S. PATENT DOCUMENTS

| | | | |
|---|---|---|---|
| 2,593,146 A | 4/1952 | Howard | |
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 3,960,494 A | 6/1976 | Verma et al. | |
| 4,100,324 A | 7/1978 | Anderson et al. | |
| 4,285,343 A | 8/1981 | McNair | |
| RE30,797 E | 11/1981 | Davis | |
| 4,323,534 A | 4/1982 | DesMarais | |
| 4,340,563 A | 7/1982 | Appel et al. | |

(Continued)

FOREIGN PATENT DOCUMENTS

EP    0282287 B2    9/1988

(Continued)

OTHER PUBLICATIONS

Abstract of Japanese Patent No. JP03195562, Aug. 27, 1991.

(Continued)

*Primary Examiner*—Melanie J Hand
(74) *Attorney, Agent, or Firm*—Dority & Manning, P.A.

(57) ABSTRACT

An odor control substrate that is applied with an activated carbon ink is provided. The activated carbon ink is applied in a pattern that covers from about 25% to about 95% of the surface area of the substrate. Although not covering the entire surface, the present inventors have discovered that the activated carbon ink is still capable of providing good odor reduction qualities to the substrate. To further enhance the aesthetic appeal of the odor control substrate to a consumer, one or more colored inks may also be applied the substrate in a pattern that may or may not overlap with the activated carbon ink pattern. The colored ink(s) may contrast well with the activated carbon ink to provide an overall design that is more aesthetically than otherwise would be provided by a uniform coating of activated carbon ink.

28 Claims, 5 Drawing Sheets

U.S. PATENT DOCUMENTS

| | | |
|---|---|---|
| 4,341,216 A | 7/1982 | Obenour |
| 4,407,960 A | 10/1983 | Tratnyek |
| 4,517,308 A | 5/1985 | Ehlenz et al. |
| 4,608,047 A | 8/1986 | Mattingly |
| 4,663,220 A | 5/1987 | Wisneski et al. |
| 4,687,478 A | 8/1987 | Van Tilburg |
| 4,758,239 A | 7/1988 | Yeo et al. |
| 4,795,668 A | 1/1989 | Krueger et al. |
| 4,802,473 A | 2/1989 | Hubbard et al. |
| 4,834,738 A | 5/1989 | Kielpikowski et al. |
| 4,950,264 A | 8/1990 | Osborn, III |
| 4,952,552 A | 8/1990 | Chapman et al. |
| 4,969,457 A | 11/1990 | Hubbard et al. |
| 4,978,615 A | 12/1990 | Aoyama et al. |
| 5,009,653 A | 4/1991 | Osborn, III |
| 5,020,533 A | 6/1991 | Hubbard et al. |
| 5,057,368 A | 10/1991 | Largman et al. |
| 5,069,970 A | 12/1991 | Largman et al. |
| 5,085,654 A | 2/1992 | Buell |
| 5,093,422 A | 3/1992 | Himes |
| 5,108,739 A | 4/1992 | Kurihara et al. |
| 5,108,820 A | 4/1992 | Kaneko et al. |
| 5,162,074 A | 11/1992 | Hills |
| 5,183,656 A | 2/1993 | Uesaka et al. |
| 5,190,563 A | 3/1993 | Herron et al. |
| 5,197,959 A | 3/1993 | Buell |
| 5,209,998 A | 5/1993 | Kavassalis et al. |
| 5,267,992 A | 12/1993 | Van Tilburg |
| 5,272,236 A | 12/1993 | Lai et al. |
| 5,277,976 A | 1/1994 | Hogle et al. |
| 5,278,272 A | 1/1994 | Lai et al. |
| 5,284,703 A | 2/1994 | Everhart et al. |
| 5,304,599 A | 4/1994 | Himes |
| 5,308,346 A | 5/1994 | Sneller et al. |
| 5,322,061 A | 6/1994 | Brunson |
| 5,332,613 A | 7/1994 | Taylor et al. |
| 5,336,552 A | 8/1994 | Strack et al. |
| 5,342,342 A | 8/1994 | Kitaoka |
| 5,350,624 A | 9/1994 | Georger et al. |
| 5,382,400 A | 1/1995 | Pike et al. |
| 5,383,450 A | 1/1995 | Hubbard et al. |
| 5,407,442 A | 4/1995 | Karapasha |
| 5,454,864 A * | 10/1995 | Whalen-Shaw ............. 106/416 |
| 5,466,410 A | 11/1995 | Hills |
| 5,503,076 A | 4/1996 | Yeo |
| 5,509,914 A | 4/1996 | Osborn, III |
| 5,539,056 A | 7/1996 | Yang et al. |
| 5,553,608 A | 9/1996 | Reese et al. |
| 5,569,234 A | 10/1996 | Buell et al. |
| 5,596,052 A | 1/1997 | Resconi et al. |
| 5,628,737 A | 5/1997 | Dobrin et al. |
| 5,634,916 A | 6/1997 | Lavon et al. |
| 5,649,916 A | 7/1997 | DiPalma et al. |
| 5,681,380 A | 10/1997 | Nohr et al. |
| 5,693,385 A | 12/1997 | Parks |
| 5,702,378 A | 12/1997 | Widlund et al. |
| 5,716,349 A | 2/1998 | Taylor et al. |
| 5,733,272 A | 3/1998 | Brunner et al. |
| 5,813,398 A | 9/1998 | Baird et al. |
| 5,834,114 A | 11/1998 | Economy et al. |
| 5,836,932 A | 11/1998 | Buell et al. |
| 5,843,057 A | 12/1998 | McCormack |
| 5,855,999 A | 1/1999 | McCormack |
| 5,861,144 A | 1/1999 | Peterson et al. |
| 5,874,067 A | 2/1999 | Lucas et al. |
| 5,932,497 A | 8/1999 | Morman et al. |
| 5,948,398 A | 9/1999 | Hanamoto et al. |
| 5,997,981 A | 12/1999 | McCormack et al. |
| 6,002,064 A | 12/1999 | Kobylivker et al. |
| 6,015,764 A | 1/2000 | McCormack et al. |
| 6,037,281 A | 3/2000 | Mathis et al. |
| 6,096,299 A | 8/2000 | Guarracino et al. |
| 6,110,158 A | 8/2000 | Kielpikowski |
| 6,111,163 A | 8/2000 | McCormack et al. |
| 6,114,024 A | 9/2000 | Forte |
| 6,153,209 A | 11/2000 | Vega et al. |
| 6,198,018 B1 | 3/2001 | Curro |
| 6,200,669 B1 | 3/2001 | Marmon et al. |
| 6,203,810 B1 | 3/2001 | Alemany et al. |
| 6,231,719 B1 | 5/2001 | Garvey et al. |
| 6,254,401 B1 | 7/2001 | Lee |
| 6,344,218 B1 | 2/2002 | Dodd et al. |
| 6,358,537 B1 | 3/2002 | Hoshino et al. |
| 6,380,455 B1 | 4/2002 | Moder et al. |
| 6,427,693 B1 | 8/2002 | Blackstock et al. |
| 6,436,128 B1 | 8/2002 | Usui |
| 6,460,989 B1 | 10/2002 | Yano et al. |
| 6,461,457 B1 | 10/2002 | Taylor et al. |
| 6,467,897 B1 | 10/2002 | Wu et al. |
| 6,475,601 B1 | 11/2002 | Sakaki et al. |
| 6,479,150 B1 | 11/2002 | Liu et al. |
| 6,517,199 B1 * | 2/2003 | Tomioka et al. ............. 347/101 |
| 6,517,906 B1 | 2/2003 | Economy et al. |
| 6,524,379 B2 | 2/2003 | Norb et al. |
| 6,536,890 B1 | 3/2003 | Kato et al. |
| 6,573,212 B2 * | 6/2003 | McCrae et al. ............. 502/180 |
| 6,639,004 B2 | 10/2003 | Falat et al. |
| 6,663,611 B2 | 12/2003 | Blaney et al. |
| 6,680,289 B1 | 1/2004 | Woo et al. |
| 6,716,203 B2 | 4/2004 | Sorebo et al. |
| 6,740,406 B2 | 5/2004 | Hu et al. |
| 6,794,024 B1 | 9/2004 | Walton et al. |
| 2002/0149656 A1 | 10/2002 | Nohr et al. |
| 2003/0116462 A1 | 6/2003 | Sorebo et al. |
| 2004/0043688 A1 | 3/2004 | Soerens et al. |
| 2004/0120904 A1 * | 6/2004 | Lye et al. ...................... 424/59 |
| 2004/0121681 A1 | 6/2004 | Lindsay et al. |
| 2004/0121688 A1 | 6/2004 | Edens et al. |
| 2004/0122386 A1 * | 6/2004 | Mocadlo ..................... 604/359 |
| 2004/0122387 A1 | 6/2004 | Long et al. |
| 2004/0122399 A1 | 6/2004 | McDaniel |
| 2004/0142159 A1 * | 7/2004 | Pallotta et al. ........... 428/295.1 |
| 2004/0166248 A1 | 8/2004 | Hu et al. |
| 2004/0176736 A1 | 9/2004 | Christon et al. |
| 2005/0142966 A1 * | 6/2005 | Quincy et al. ................. 442/72 |

FOREIGN PATENT DOCUMENTS

| | | |
|---|---|---|
| EP | 0348978 A2 | 1/1990 |
| EP | 0389015 A2 | 9/1990 |
| EP | 0389015 A3 | 9/1990 |
| EP | 0510619 A1 | 10/1992 |
| EP | 0749295 B1 | 12/1996 |
| EP | 1034800 A1 | 9/2000 |
| EP | 1188854 A1 | 3/2002 |
| WO | WO 9112029 A1 | 8/1991 |
| WO | WO 9112030 A1 | 8/1991 |
| WO | WO 9820915 A1 | 5/1998 |
| WO | WO 9826808 A2 | 6/1998 |
| WO | WO 9826808 A3 | 6/1998 |
| WO | WO 9900093 A1 | 1/1999 |
| WO | WO 9912734 A1 | 3/1999 |
| WO | WO 02055115 A1 | 7/2002 |
| WO | WO 02094329 A1 | 11/2002 |
| WO | WO 03000979 A2 | 1/2003 |

OTHER PUBLICATIONS

Abstract of Japanese Patent No. JP03221142, Sep. 30, 1991.
Abstract of Japanese Patent No. JP06285140, Oct. 11, 1994.
Article—*Adsorption of Dyes on Nanosize Modified Silica Particles*, Guangwei Wu, Athanasia Koliadima, Yie-Shein Her, and Egon Matijevic, Journal of Colloid and Interface Science, vol. 195, 1997, pp. 222-228.

Article—*Adsorption Of Gases In Multimolecular Layers*, Stephen Brunauer, P. H. Emmett, and Edward Teller, The Journal of the American Chemical Society, vol. 60, Feb. 1938, pp. 309-319.

Pocket Guide to Digital Printing, Frank Cost, Delmar Publishers, Albany, NY, ISBN 0-8273-7592-1, pp. 144-145.

Fish, et al. U.S. Appl. No. 10/687,425, filed Oct. 16, 2003, Odor Absorbing Extrudates.

MacDonald, et al., U.S. Appl. No. 10/687,269, filed Oct. 16, 2003, Odor Controlling Article Including A Visual Indicating Device For Monitoring Odor Absorption.

Quincy, III et al., U.S. Appl. No. 10/723,761, filed Nov. 26, 2003, Odor Control In Personal Care Products.

Quincy, III et al., U.S. Appl. No. 10/749,689, filed Dec. 31, 2003, Odor Control Materials And Face Masks Including Odor Control Materials.

MacDonald et al., U.S. Appl. No. 10/955,316, filed Sep. 30, 2004, Odor-Reducing Quinone Compounds.

MacDonald et al., U.S. Appl. No. 11/021,571, filed Dec. 23, 2004, Odor Control Substrates.

Roger B. Quincy, III, U.S. Appl. No. 11/021,547, filed Dec. 23, 2004, Activated Carbon Substrates.

* cited by examiner

PATTERNED APPLICATION OF ACTIVATED CARBON INK

BACKGROUND OF THE INVENTION

Odor control additives have been conventionally incorporated into substrates for a variety of reasons. For instance, absorbent articles may contain odor control additives to absorb compounds that result in the production of malodors contained in absorbed fluids or their degradation products. Examples of these compounds include fatty acids, ammonia, amines, sulfur-containing compounds, ketones and aldehydes. Various types of odor control additives have been employed for this purpose. For instance, activated carbon has been used to reduce a broad spectrum of odors. In spite of its excellent properties as an adsorbent, the use of activated carbon in disposable absorbent articles has been limited by its black color. That is, many consumers associate the traditionally black color of activated carbon with a dirty or grimy material.

As such, a need currently exists for odor control substrates that are capable of achieving reducing odor, and yet also aesthetically pleasing to a consumer.

SUMMARY OF THE INVENTION

In accordance with one embodiment of the present invention, a method for forming an odor control substrate is disclosed. The method comprises forming a first ink that comprises activated carbon, a binder, and a solvent. The first ink is printed onto a surface of the substrate so that it covers from about 25% to about 95% of the area of the surface. The first ink is dried and has a solids add-on level of at least about 2%. The first ink also presents a color (e.g., black) that is visually distinguishable from another color presented by the substrate. If desired, a second ink may also be printed onto the substrate that presents a color that is visually distinguishable from the color of the first ink. For example, the color of the second ink may be white, yellow, cyan, magenta, red, green, blue, or combinations thereof. The first and second inks may be applied in an overlapping and/or non-overlapping relationship.

In accordance with another embodiment of the present invention, an odor control substrate is disclosed that is applied with a first ink and a second ink, the first ink comprising activated carbon. The first ink covers from about 30% to about 90% of the area of a surface of the substrate and is present at a solids add-on level of at least about 2%. The first ink presents a color that is visually distinguishable from the color of the second ink.

In accordance with still another embodiment of the present invention, a pouch for individually wrapping a feminine care absorbent article is disclosed. The pouch comprises a wrapper having an inner surface. The inner surface is applied with a first ink that comprises activated carbon. The first ink covers from about 25% to about 95% of the area of the inner surface. The first ink presents a color that is visually distinguishable from another color presented by the wrapper.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which:

FIG. 1 illustrates an odor control substrate having overlapping color patterns in accordance with one embodiment of the present invention, in which FIG. 1A depicts a colored ink printed on top of an activated carbon ink and in which

Figure 1A:
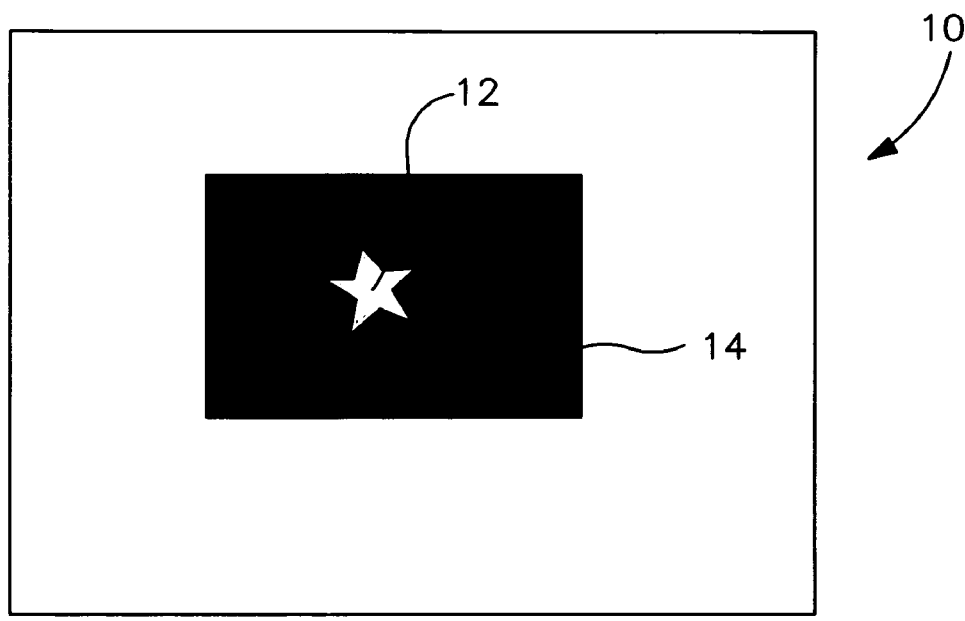

Repeat use of reference characters in the present specification and drawings is intended to represent same or analogous features or elements of the invention.

DETAILED DESCRIPTION OF THE REPRESENTATIVE EMBODIMENTS

Definitions

As used herein the term "nonwoven fabric or web" refers to a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, etc.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 20 microns.

As used herein, the term "coform" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

As used herein, the term "multicomponent fibers" generally refers to fibers that have been formed from at least two polymer components. Such fibers are typically extruded from separate extruders, but spun together to form one fiber. The polymers of the respective components are typically different, but may also include separate components of similar or identical polymeric materials. The individual components are typically arranged in substantially constantly positioned distinct zones across the cross-section of the fiber and extend substantially along the entire length of the fiber. The configuration of such fibers may be, for example, a side-by-side arrangement, a pie arrangement, or any other arrangement. Multicomponent fibers and methods of making the same are taught in U.S. Pat. No. 5,108,820 to Kaneko, et al., U.S. Pat. No. 4,795,668 to Kruege. et al., U.S. Pat. No. 5,382,400 to Pike, et al., U.S. Pat. No. 5,336,552 to Strack, et al., and U.S. Pat. No. 6,200,669 to Marmon, et al., which are incorporated herein in their entirety by reference thereto for all purposes. The fibers and individual components containing the same may also have various irregular shapes such as those described in U.S. Pat. No. 5,277,976 to Hogle, et al., U.S. Pat. No. 5,162,074 to Hills, U.S. Pat. No. 5,466,410 to Hills, U.S. Pat. No. 5,069,970 to Largman, et al., and U.S. Pat. No. 5,057,368 to Larqman, et al., which are incorporated herein in their entirety by reference thereto for all purposes.

As used herein, the term "elastomeric" and "elastic" and refers to a material that, upon application of a stretching force, is stretchable in at least one direction (such as the CD direction), and which upon release of the stretching force, contracts/returns to approximately its original dimension. For example, a stretched material may have a stretched length that is at least 50% greater than its relaxed unstretched length, and which will recover to within at least 50% of its stretched length upon release of the stretching force. A hypothetical example would be a one (1) inch sample of a material that is stretchable to at least 1.50 inches and which, upon release of the stretching force, will recover to a length of not more than 1.25 inches. Desirably, such elastomeric sheet contracts or recovers at least 50%, and even more desirably, at least 80% of the stretch length in the cross machine direction.

As used herein, the term "breathable" means pervious to water vapor and gases, but impermeable to liquid water. For instance, "breathable barriers" and "breathable films" allow water vapor to pass therethrough, but are substantially impervious to liquid water. The "breathability" of a material is measured in terms of water vapor transmission rate (WVTR), with higher values representing a more vapor-pervious material and lower values representing a less vapor-pervious material. Typically, the "breathable" materials have a water vapor transmission rate (WVTR) of from about 500 to about 20,000 grams per square meter per 24 hours ($g/m^2/24$ hours), in some embodiments from about 1,000 to about 15,000 $g/m^2/24$ hours, and in some embodiments, from about 1,500 to about 14,000 $g/m^2/24$ hours.

As used herein, an "absorbent article" refers to any article capable of absorbing water or other fluids. Examples of some absorbent articles include, but are not limited to, personal care absorbent articles, such as diapers, training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth. Materials and processes suitable for forming such absorbent articles are well known to those skilled in the art.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

In general, the present invention is directed to an odor control substrate that is applied with an activated carbon ink. The activated carbon ink is applied in a pattern that covers from about 25% to about 95% of the surface area of the substrate. Although not covering the entire surface, the present inventors have discovered that the activated carbon ink is still capable of providing good odor reduction qualities to the substrate. To further enhance the aesthetic appeal of the odor control substrate to a consumer, one or more colored inks may also be applied the substrate in a pattern that may or may not overlap with the activated carbon ink pattern. The colored ink(s) may contrast well with the activated carbon ink to provide an overall design that is more aesthetically than otherwise would be provided by a uniform coating of activated carbon ink.

A. Substrates

Any of variety of substrates may be applied with an activated carbon ink in accordance with the present invention. For example, nonwoven webs, woven fabrics, knit fabrics, films, and so forth, may be employed. In most embodiments, the substrate contains at least one nonwoven web. When utilized, the nonwoven web may include, but not limited to, spunbond webs, meltblown webs, bonded carded webs, air-laid webs, coform webs, hydraulically entangled webs, and so forth. Nonwoven webs may be formed by a variety of different materials. For instance, suitable polymers for forming nonwoven webs may include polyolefins, polyamides, polyesters, polycarbonates, polystyrenes, thermoplastic elastomers, fluoropolymers, vinyl polymers, and blends and copolymers thereof. Suitable polyolefins include, but are not limited to, polyethylene, polypropylene, polybutylene, and so forth; suitable polyamides include, but are not limited to, nylon 6, nylon 6/6, nylon 10, nylon 12 and so forth; and suitable polyesters include, but are not limited to, polyethylene terephthalate, polybutylene terephthalate, polytrimethyl terephthalate, polylactic acid, and so forth. Particularly suitable polymers for use in the present invention are polyolefins including polyethylene, for example, linear low density polyethylene, low density polyethylene, medium density polyethylene, and high density polyethylene; polypropylene; polybutylene; as well as copolymers and blends thereof.

The fibers used to form the nonwoven web may be in the form of substantially continuous fibers, staple fibers, and so forth. Substantially continuous fibers, for example, may be produced by known nonwoven extrusion processes, such as, for example, known solvent spinning or melt-spinning processes. In one embodiment, the nonwoven web contains substantially continuous melt-spun fibers formed by a spunbond process. The spunbond fibers may be formed from any melt-spinnable polymer, co-polymers or blends thereof. The denier of the fibers used to form the nonwoven web may also vary. For instance, in one particular embodiment, the denier of polyolefin fibers used to form the nonwoven web is less than about 6, in some embodiments less than about 3, and in some embodiments, from about 1 to about 3. In one particular embodiment of the present invention, multicomponent (e.g., bicomponent) fibers are utilized. For example, suitable configurations for the multicomponent fibers include side-by-side configurations and sheath-core configurations, and suitable sheath-core configurations include eccentric sheath-core and concentric sheath-core configurations. In some embodiments, as is well known in the art, the polymers used to form the multicomponent fibers have sufficiently different melting points to form different crystallization and/or solidification properties. The multicomponent fibers may have from about 20% to about 80%, and in some embodiments, from about 40% to about 60% by weight of the low melting polymer. Further, the multicomponent fibers may have from about 80% to about 20%, and in some embodiments, from about 60% to about 40%, by weight of the high melting polymer.

As stated above, a film may also be utilized to form the substrate. To form a film, a variety of materials may be utilized. For instance, some suitable thermoplastic polymers used in the fabrication of films may include, but are not limited to, polyolefins (e.g., polyethylene, polypropylene, etc.), including homopolymers, copolymers, terpolymers and blends thereof; ethylene vinyl acetate; ethylene ethyl acrylate; ethylene acrylic acid; ethylene methyl acrylate; ethylene normal butyl acrylate; polyurethane; poly(ether-ester); poly (amid-ether) block copolymers; and so forth.

In one particular embodiment, the film may be made a liquid-impermeable plastic film, such as a polyethylene and polypropylene film. Generally, such plastic films are impermeable to gases and water vapor, as well as liquids. In addition, the film may be impermeable to liquids, but permeable to gases and water vapor (i.e., "breathable"). Such breathable films are useful in a variety of articles, such as in an outer cover of an absorbent article to permit vapors to escape from the absorbent core, but prevent liquid exudates from passing therethrough. The breathable film may be microporous or monolithic. In microporous films, the micropores form what is often referred to as tortuous pathways through the film. Liquid contacting one side of the film does not have a direct passage through the film. Instead, a network of microporous channels in the film prevents liquids from passing, but allows gases and water vapor to pass. Microporous films may be formed from a polymer and a filler (e.g., calcium carbonate). Fillers are particulates or other forms of material that may be added to the film polymer extrusion blend and that will not chemically interfere with the extruded film, but which may be uniformly dispersed throughout the film. Generally, on a dry weight basis, based on the total weight of the film, the film includes from about 30% to about 90% by weight of a polymer. In some embodiments, the film includes from about 30% to about 90% by weight of a filler. Examples of such films are described in U.S. Pat. No. 5,843,057 to McCormack; U.S. Pat. No. 5,855,999 to McCormack; U.S. Pat. No. 5,932,497 to Morman. et al.; U.S. Pat. No. 5,997,981 to McCormack et al.; U.S. Pat. No. 6,002,064 to Kobvlivker, et al.; U.S. Pat. No. 6,015,764 to McCormack, et al.; U.S. Pat. No. 6,037,281 to Mathis, et al.; U.S. Pat. No. 6,111,163 to McCormack, et al.; and U.S. Pat. No. 6,461,457 to Taylor, et al., which are incorporated herein in their entirety by reference thereto for all purposes.

The films are generally made breathable by stretching the filled films to create the microporous passageways as the polymer breaks away from the calcium carbonate during stretching. For example, the breathable material contains a stretch-thinned film that includes at least two basic components, i.e., a polyolefin polymer and filler. These components are mixed together, heated, and then extruded into a film layer using any one of a variety of film-producing processes known to those of ordinary skill in the film processing art. Such film-making processes include, for example, cast embossed, chill and flat cast, and blown film processes.

Another type of breathable film is a monolithic film that is a nonporous, continuous film, which because of its molecular structure, is capable of forming a liquid-impermeable, vapor-permeable barrier. Among the various polymeric films that fall into this type include films made from a sufficient amount of poly(vinyl alcohol), polyvinyl acetate, ethylene vinyl alcohol, polyurethane, ethylene methyl acrylate, and ethylene methyl acrylic acid to make them breathable. Without intending to be held to a particular mechanism of operation, it is believed that films made from such polymers solubilize water molecules and allow transportation of those molecules from one surface of the film to the other. Accordingly, these films may be sufficiently continuous, i.e., nonporous, to make them substantially liquid-impermeable, but still allow for vapor permeability.

Breathable films, such as described above, may constitute the entire breathable material, or may be part of a multilayer film. Multilayer films may be prepared by cast or blown film coextrusion of the layers, by extrusion coating, or by any conventional layering process. Further, other breathable materials that may be suitable for use in the present invention are described in U.S. Pat. No. 4,341,216 to Obenour; U.S. Pat. No. 4,758,239 to Yeo, et al.; U.S. Pat. No. 5,628,737 to Dobrin, et al.; U.S. Pat. No. 5,836,932 to Buell; U.S. Pat. No. 6,114,024 to Forte; U.S. Pat. No. 6,153,209 to Vega, et al.; U.S. Pat. No. 6,198,018 to Curro; U.S. Pat. No. 6,203,810 to Alemany, et al.; and U.S. Pat. No. 6,245,401 to Ying, et al., which are incorporated herein in their entirety by reference thereto for all purposes.

If desired, the breathable film may also be bonded to a nonwoven web, knitted fabric, and/or woven fabric using well-known techniques. For instance, suitable techniques for bonding a film to a nonwoven web are described in U.S. Pat. No. 5,843,057 to McCormack; U.S. Pat. No. 5,855,999 to McCormack; U.S. Pat. No. 6,002,064 to Kobylivker, et al.; U.S. Pat. No. 6,037,281 to Mathis, et al.; and WO 99/12734, which are incorporated herein in their entirety by reference thereto for all purposes. For example, a breathable film/nonwoven laminate material may be formed from a nonwoven layer and a breathable film layer. The layers may be arranged so that the breathable film layer is attached to the nonwoven layer. In one particular embodiment, the breathable material is formed from a nonwoven fabric (e.g., polypropylene spunbond web) laminated to a breathable film.

The substrate may also contain an elastomeric polymer, such as elastomeric polyesters, elastomeric polyurethanes, elastomeric polyamides, elastomeric polyolefins, elastomeric copolymers, and so forth. Examples of elastomeric copolymers include block copolymers having the general formula A-B-A' or A-B, wherein A and A' are each a thermoplastic polymer endblock that contains a styrenic moiety and B is an elastomeric polymer midblock, such as a conjugated diene or a lower alkene polymer. Such copolymers may include, for instance, styrene-isoprene-styrene (S-I-S), styrene-butadiene-styrene (S-B-S), styrene-ethylene-butylene-styrene (S-EB-S), styrene-isoprene (S-I), styrene-butadiene (S-B), and so forth. Commercially available A-B-A' and A-B-A-B copolymers include several different S-EB-S formulations from Kraton Polymers of Houston, Tex. under the trade designation KRATON®. KRATON® block copolymers are available in several different formulations, a number of which are identified in U.S. Pat. Nos. 4,663,220, 4,323,534, 4,834,738, 5,093,422 and 5,304,599, which are hereby incorporated in their entirety by reference thereto for all purposes. Other commercially available block copolymers include the S-EP-S elastomeric copolymers available from Kuraray Company, Ltd. of Okayama, Japan, under the trade designation SEPTON®. Still other suitable copolymers include the S-I-S and S-B-S elastomeric copolymers available from Dexco Polymers of Houston, Tex. under the trade designation VECTOR®. Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer.

Examples of elastomeric polyolefins include ultra-low density elastomeric polypropylenes and polyethylenes, such as those produced by "single-site" or "metallocene" catalysis methods. Such elastomeric olefin polymers are commercially available from ExxonMobil Chemical Co. of Houston, Tex. under the trade designations ACHIEVE® (propylene-based), EXACT® (ethylene-based), and EXCEED® (ethylene-based). Elastomeric olefin polymers are also commercially available from DuPont Dow Elastomers, LLC (a joint venture between DuPont and the Dow Chemical Co.) under the trade designation ENGAGE® (ethylene-based) and from Dow Chemical Co. of Midland, Mich. under the name AFFINITY® (ethylene-based). Examples of such polymers are also described in U.S. Pat. Nos. 5,278,272 and 5,272,236 to Lai, et al., which are incorporated herein in their entirety by reference thereto for all purposes. Also useful are certain elastomeric polypropylenes, such as described in U.S. Pat. No. 5,539,056 to Yanq, et al. and U.S. Pat. No. 5,596,052 to Resconi, et al., which are incorporated herein in their entirety by reference thereto for all purposes.

If desired, blends of two or more polymers may also be utilized. For example, a blend of a high performance elastomer and a lower performance elastomer may be utilized. A high performance elastomer is generally an elastomer having a low level of hysteresis, such as less than about 75%, and in some embodiments, less than about 60%. Likewise, a low performance elastomer is generally an elastomer having a high level of hysteresis, such as greater than about 75%. Particularly suitable high performance elastomers may include styrenic-based block copolymers, such as described above and commercially available from Kraton Polymers under the trade designation KRATON® and from Dexco Polymers under the trade designation VECTOR®. Likewise, particularly suitable low performance elastomers include elastomeric polyolefins, such as metallocene-catalyzed polyolefins (e.g., single site metallocene-catalyzed linear low density polyethylene) commercially available from Dow Chemical Co. under the trade designation AFFINITY®. In some embodiments, the high performance elastomer may constitute from about 25 wt. % to about 90 wt. % of the blend, and the low performance elastomer may likewise constitute from about 10 wt. % to about 75 wt. % of the blend. Further examples of such a high performance/low performance elastomer blend are described in U.S. Pat. No. 6,794,024 to Walton, et al., which is incorporated herein in its entirety by reference thereto for all purposes.

B. Activated Carbon Inks

Regardless of the particular substrate selected, an activated carbon ink is applied to the substrate for reducing odor. When applied in accordance with the present invention, the ink is also durable and present in an aesthetically pleasing pattern on the substrate. Generally speaking, activated carbon may be derived from a variety of sources, such as from sawdust, wood, charcoal, peat, lignite, bituminous coal, coconut shells, etc. Some suitable forms of activated carbon and techniques for formation thereof are described in U.S. Pat. No. 5,693,385 to Parks; U.S. Pat. No. 5,834,114 to Economy, et al.; U.S. Pat. No. 6,517,906 to Economy, et al.; U.S. Pat. No. 6,573,212 to McCrae, et al., as well as U.S. Patent Application Publication Nos. 2002/0141961 to Falat. et al. and 2004/0166248 to Hu, et al., all of which are incorporated herein in their entirety by reference thereto for all purposes. The concentration of activated carbon in the ink (prior to drying) is generally tailored to facilitate odor control without adversely affecting other properties of the substrate, such as flexibility, absorbency, etc. For instance, activated carbon is typically present in the ink in an amount from about 1 wt. % to about 50 wt. %, in some embodiments from about 5 wt. % to about 25 wt. %, and in some embodiments, from about 10 wt. % to about 20 wt. %.

The activated carbon ink also generally contains a binder for increasing the durability of the activated carbon when applied to a substrate, even when present at high levels. The binder may also serve as an adhesive for bonding one substrate to another substrate. Generally speaking, any of a variety of binders may be used in the activated carbon ink of the present invention. Suitable binders may include, for instance, those that become insoluble in water upon crosslinking. Crosslinking may be achieved in a variety of ways, including by reaction of the binder with a polyfunctional crosslinking agent. Examples of such crosslinking agents include, but are not limited to, dimethylol urea melamine-formaldehyde, urea-formaldehyde, polyamide epichlorohydrin, etc.

In some embodiments, a polymer latex may be employed as the binder. The polymer suitable for use in the lattices typically has a glass transition temperature of about 30° C. or less so that the flexibility of the resulting substrate is not substantially restricted. Moreover, the polymer also typically has a glass transition temperature of about −25° C. or more to minimize the tackiness of the polymer latex. For instance, in some embodiments, the polymer has a glass transition temperature from about −15° C. to about 15° C., and in some embodiments, from about −10° C. to about 0° C. For instance, some suitable polymer lattices that may be utilized in the present invention may be based on polymers such as, but are not limited to, styrene-butadiene copolymers, polyvinyl acetate homopolymers, vinyl-acetate ethylene copolymers, vinyl-acetate acrylic copolymers, ethylene-vinyl chloride copolymers, ethylene-vinyl chloride-vinyl acetate terpolymers, acrylic polyvinyl chloride polymers, acrylic polymers, nitrile polymers, and any other suitable anionic polymer latex polymers known in the art. The charge of the polymer lattices described above may be readily varied, as is well known in the art, by utilizing a stabilizing agent having the desired charge during preparation of the polymer latex. For instance, specific techniques for an activated carbon/polymer latex system are described in more detail in U.S. Pat. No. 6,573,212 to McCrae, et al. Activated carbon/polymer latex systems that may be used in the present invention include Nuchar® PMA, DPX-8433-68A, and DPX-8433-68B, all of which are made by MeadWestvaco Corp of Covington, Va.

Although polymer lattices may be effectively used as binders in the present invention, such compounds sometimes result in a reduction in drapability and an increase in residual odor. Thus, water-soluble organic polymers may also be employed as binders to alleviate such concerns. Another benefit of the water-soluble binder of the present invention is that it may facilitate the controlled release of the activated carbon ink from the substrate in an aqueous environment. Specifically, upon contacting an aqueous solution, the water-soluble binder dissolves and loses some of its binding qualities, thereby allowing other components of the activated carbon ink to be released from the substrate. This may be useful in various applications, such as for hard-surface wipers in which it is desired for the activated carbon ink to be released into the wiped environment for sustained odor control.

One class of water-soluble organic polymers found to be suitable in the present invention is polysaccharides and derivatives thereof. Polysaccharides are polymers containing repeated carbohydrate units, which may be cationic, anionic, nonionic, and/or amphoteric. In one particular embodiment, the polysaccharide is a nonionic, cationic, anionic, and/or amphoteric cellulosic ether. Suitable nonionic cellulosic ethers may include, but are not limited to, alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, methyl hydroxypropyl cellulose, ethyl hydroxyethyl cellulose, ethyl hydroxypropyl cellulose, methyl ethyl hydroxyethyl cellulose and methyl ethyl hydroxypropyl cellulose; and so forth.

Suitable cellulosic ethers may include, for instance, those available from Akzo Nobel of Covington, Virginia under the name "BERMOCOLL." Still other suitable cellulosic ethers are those available from Shin-Etsu Chemical Co., Ltd. of Tokyo, Japan under the name "METOLOSE", including METOLOSE Type SM (methycellulose), METOLOSE Type SH (hydroxypropylmethyl cellulose), and METOLOSE Type SE (hydroxyethylmethyl cellulose). One particular example of a suitable nonionic cellulosic ether is ethyl hydroxyethyl cellulose having a degree of ethyl substitution (DS) of 0.8 to 1.3 and a molar substitution (MS) of hydroxyethyl of 1.9 to 2.9. The degree of ethyl substitution represents the average number of hydroxyl groups present on each anhydroglucose unit that have been reacted, which may vary between 0 and 3. The molar substitution represents the average number of hydroxyethyl groups that have reacted with each anhydroglucose unit. One such cellulosic ether is BERMOCOLL E 230FQ, which is an ethyl hydroxyethyl cellulose commercially available from Akzo Nobel. Other suitable cellulosic ethers are also available from Hercules, Inc. of Wilmington, Del. under the name "CULMINAL."

The total concentration of the binders may generally vary depending on the desired properties of the resulting substrate. For instance, high total binder concentrations may provide better physical properties for the coated substrate, but may likewise have an adverse affect on other properties, such as the absorptive capacity or extensibility of the substrate to which it is applied. Conversely, low total binder concentrations may not provide the desired degree of durability. Thus, in most embodiments, the total amount of binder employed in the activated carbon ink (prior to drying) is from about 0.01 wt. % to about 30 wt. %, in some embodiments from about 0.1 wt. % to about 20 wt. %, and in some embodiments, from about 1 wt. % to about 15 wt. %.

Besides the above-mentioned components, a masking agent may also be employed in the activated carbon ink to further alter the aesthetic properties of the substrate. That is, the masking agent may enhance opacity and/or alter the color to the ink. To provide optimum masking effects, the size of the particles is desirably less than the size of any activated carbon particles employed. For example, the masking particles may have a size less than about 100 micrometers, in some embodiments less than about 50 micrometers, and in some embodiments, less than about 25 micrometers. For example, activated carbon particles may sometimes have a particle size of approximately 35 micrometers. In such cases, the size of the masking particles is typically less than 35 micrometers, and preferably much smaller, such as less than about 10 micrometers. Likewise, the particles may be porous. Without intending to be limited by theory, it is believed that porous particles may provide a passage for odorous compounds to better contact the odor adsorbent. For example, the particles may have pores/channels with a mean diameter of greater than about 5 angstroms, in some embodiments greater than about 20 angstroms, and in some embodiments, greater than about 50 angstroms. The surface area of such particles may also be greater than about 15 square meters per gram, in some embodiments greater than about 25 square meters per gram, and in some embodiments, greater than about 50 square meters per gram. Surface area may be determined by the physical gas adsorption (B.E.T.) method of Bruanauer, Emmet, and Teller, *Journal of American Chemical Society*, Vol. 60, 1938, p. 309, with nitrogen as the adsorption gas.

In one particular embodiment, porous carbonate particles (e.g., calcium carbonate) are used to alter the black color normally associated with activated carbon. Such a color change may be more aesthetically pleasing to a user, particularly when the coating is employed on substrates designed for consumer/personal use. Suitable white calcium carbonate particles are commercially available from Omya, Inc. of Proctor, Vermont. Still other suitable particles include, but are not limited to, silicates, such as calcium silicate, alumina silicates (e.g., mica powder, clay, etc.), magnesium silicates (e.g., talc), quartzite, calcium silicate fluorite, etc.; alumina; silica; and so forth. The concentration of the particles may generally vary depending on the nature of the particles, and the desired extent of odor control and color alteration. For instance, the particles may be present in the ink (prior to drying) in an amount from about 0.01 wt. % to about 30 wt. %, in some embodiments from about 0.1 wt. % to about 20 wt. %, and in some embodiments, from about 1 wt. % to about 15 wt. %.

Other compounds, such as surfactants, electrolytic salts, pH adjusters, etc., may also be included in the activated carbon ink of the present invention. Although not required, such additional components typically constitute less than about 5 wt. %, in some embodiments less than about 2 wt. %, and in some embodiments, from about 0.001 wt. % to about 1 wt. % of the activated carbon ink (prior to drying). For example, as is well known in the art, an electrolytic salt may be employed to control the gelation temperature of a water-soluble binder. Suitable electrolytic salts may include, but are not limited to, alkali halides or sulfates, such as sodium chloride, potassium chloride, etc.; alkaline halides or sulfates, such as calcium chloride, magnesium chloride, etc., and so forth.

To form the activated carbon ink, its components are first typically dissolved or dispersed in a solvent. For example, one or more of the above-mentioned components may be mixed with a solvent, either sequentially or simultaneously, to form an ink formulation that may be easily applied to a substrate. Any solvent capable of dispersing or dissolving the components is suitable, for example water; alcohols such as ethanol or methanol; dimethylformamide; dimethyl sulfoxide; hydrocarbons such as pentane, butane, heptane, hexane, toluene and xylene; ethers such as diethyl ether and tetrahydrofuran; ketones and aldehydes such as acetone and methyl ethyl ketone; acids such as acetic acid and formic acid; and halogenated solvents such as dichloromethane and carbon tetrachloride; as well as mixtures thereof. The concentration of solvent in the ink formulation is generally high enough to allow easy application, handling, etc. If the amount of solvent is too large, however, the amount of activated carbon deposited on the substrate might be too low to provide the desired odor reduction. Although the actual concentration of solvent employed will generally depend on the type of activated carbon and the substrate on which it is applied, it is nonetheless typically present in an amount from about 40 wt. % to about 99 wt. %, in some embodiments from about 50 wt. % to about 95 wt. %, and in some embodiments, from about 60 wt. % to about 90 wt. % of the ink (prior to drying).

The solids content and/or viscosity of the ink may be varied to achieve the extent of odor reduction desired. For example, the ink may have a solids content of from about 5% to about 90%, in some embodiments from about 10% to about 80%, and in some embodiments, from about 20% to about 70%. By varying the solids content of the ink, the presence of the activated carbon and other components in the activated carbon ink may be controlled. For example, to form an activated carbon ink with a higher level of activated carbon, the ink may be provided with a relatively high solids content so that a greater percentage of activated carbon is incorporated into the activated carbon ink during the application process. Generally, the viscosity is less than about $2 \times 10^6$ centipoise, in some embodiments less than about $2 \times 10^5$ centipoise, in some embodiments less than about $2 \times 10^4$ centipoise, and in some embodiments, less than about $2 \times 10^3$ centipoise, such as measured with a Brookfield viscometer, type DV-I or LV-IV, at 60 rpm and 20° C. If desired, thickeners or other viscosity modifiers may be employed in the ink to increase or decrease viscosity.

C. Ink Application

The activated carbon ink is applied to the substrate in a pattern that presents a stark and highly visible contrast against a different color, such as the color of the background. Thus, instead of being hidden within the substrate, the activated carbon ink is used to change the overall appearance of the substrate. For example, the activated carbon ink may have a dark color (e.g., black) and applied against a contrasting light background. Alternatively, a differently colored foreground may contrast with a dark background provided by the activated carbon ink. The relative degree of contrast between the odor control ink and the other color may be measured through a gray-level difference value. In a particular embodiment, the contrast may have a gray level value of about 45 on a scale of 0 to about 255, where 0 represents "black" and 255 represents "white." The analysis method may be made with a Quantimet 600 Image Analysis System (Leica, Inc., Cambridge, UK). This system's software (QWIN Version 1.06A) enables a program to be used in the Quantimet User Interactive Programming System (QUIPS) to make the gray-level determinations. A control or "blank" white-level may be set using undeveloped Polaroid photographic film. An 8-bit gray-level scale may then be used (0-255) and the program allowed the light level to be set by using the photographic film as the standard. A region containing the other color (e.g., background or foreground) may then be measured for its gray-level value, followed by the same measurement of the activate carbon ink. The routine may be programmed to automatically calculate the gray-level value of the activated carbon ink. The difference in gray-level value between the activated carbon ink and the other color may be about 45 or greater on a scale of 0-255, where 0 represents "black" and 255 represents "white."

The particular type or style of activated carbon ink pattern is not a limiting factor of the invention, and may include, for example, any arrangement of stripes, bands, dots, or other geometric shape. The pattern may include indicia (e.g., trademarks, text, and logos), floral designs, abstract designs, any configuration of artwork, etc. The pattern may be targeted for a specific class of consumers. For example, in the case of diapers or training pants, the pattern may be in the form of cartoon characters, and so forth. It should be appreciated that the "pattern" may take on virtually any desired appearance.

Nevertheless, the activated carbon ink usually covers from about 25% to about 95% of the surface area of the substrate, in some embodiments from about 30% to about 90% of the surface area of the substrate, and in some embodiments, from about 30% to about 50% of the surface area of one or more surfaces of the substrate. Not only does such a patterned application have improved aesthetic appeal in comparison to uniformly applied inks, but the present inventors have also discovered that the patterned ink may still achieve good odor reduction. The patterned application of activated carbon ink may also have various other functional benefits, including optimizing flexibility, absorbency, or some other characteristic of the substrate. The patterned application of activated carbon ink may also provide different odor control properties to multiple locations of the substrate. For example, in one embodiment, the substrate is treated with two or more regions of activated carbon ink that may or may not overlap. The regions may be on the same or different surfaces of the substrate. In one embodiment, one region of a substrate is coated with a first activated carbon ink, while another region is coated with a second activated carbon ink. If desired, one region may be configured to reduce one type of odor, while another region may be configured to reduce another type of odor. Alternatively, one region may possess a higher level of an activated carbon ink than another region or substrate to provide different levels of odor reduction.

A variety of techniques may be used for applying the activated ink in the above-described manner. For instance, the ink may be applied using rotogravure or gravure printing, either direct or indirect (offset). Gravure printing encompasses several well-known engraving techniques, such as mechanical engraving, acid-etch engraving, electronic engraving and ceramic laser engraving. Such printing techniques provide excellent control of the composition distribution and transfer rate. Gravure printing may provide, for example, from about 10 to about 1000 deposits per lineal inch of surface, or from about 100 to about 1,000,000 deposits per square inch. Each deposit results from an individual cell on a printing roll, so that the density of the deposits corresponds to the density of the cells. A suitable electronic engraved example for a primary delivery zone is about 200 deposits per lineal inch of surface, or about 40,000 deposits per square inch. By providing such a large number of small deposits, the uniformity of the deposit distribution may be enhanced. Also, because of the large number of small deposits applied to the surface of the substrate, the deposits more readily resolidify on the exposed fiber portions. Suitable gravure printing techniques are also described in U.S. Pat. No. 6,231,719 to Garvey, et al., which is incorporated herein in its entirety by reference thereto for all purposes. Moreover, besides gravure printing, it should be understood that other printing techniques, such as flexographic printing, may also be used to apply the coating.

Still another suitable contact printing technique that may be utilized in the present invention is "screen printing." Screen printing is performed manually or photomechanically. The screens may include a silk or nylon fabric mesh with, for instance, from about 40 to about 120 openings per lineal centimeter. The screen material is attached to a frame and stretched to provide a smooth surface. The stencil is applied to the bottom side of the screen, i.e., the side in contact with the substrate upon which the fluidic channels are to be printed. The ink is painted onto the screen, and transferred by rubbing the screen (which is in contact with the substrate) with a squeegee.

Ink-jet printing techniques may also be employed in the present invention. Ink-jet printing is a non-contact printing technique that involves forcing the ink through a tiny nozzle (or a series of nozzles) to form droplets that are directed toward the substrate. Two techniques are generally utilized, i.e., "DOD" (Drop-On-Demand) or "continuous" ink-jet printing. In continuous systems, ink is emitted in a continuous stream under pressure through at least one orifice or nozzle. The stream is perturbed by a pressurization actuator to break the stream into droplets at a fixed distance from the orifice. DOD systems, on the other hand, use a pressurization actuator at each orifice to break the ink into droplets. The pressurization actuator in each system may be a piezoelectric crystal, an acoustic device, a thermal device, etc. The selection of the type of ink jet system varies on the type of material to be printed from the print head. For example, conductive materials are sometimes required for continuous systems because the droplets are deflected electrostatically. Thus, when the sample channel is formed from a dielectric material, DOD printing techniques may be more desirable.

In addition to the printing techniques mentioned above, any other suitable application technique may be used in the present invention. For example, other suitable printing techniques may include, but not limited to, such as laser printing, thermal ribbon printing, piston printing, spray printing, flexographic printing, etc. Still other suitable application techniques may include bar, roll, knife, curtain, spray, slot-die, dip-coating, drop-coating, extrusion, stencil application, etc. Such techniques are well known to those skilled in the art.

Regardless of the method of application, the odor control substrate may sometimes be dried at a certain temperature to drive the solvent from the activated carbon ink. For example, the substrate may be heated to a temperature of at least about 50° C., in some embodiments at least about 70° C., and in some embodiments, at least about 80° C. By minimizing the amount of solvent in the activated carbon ink, a larger surface area of activated carbon may be available for contacting odorous compounds, thereby enhancing odor reduction. It should be understood, however, that relatively small amounts of solvent may still be present. For example, the dried ink may contain a solvent in an amount less than about 10% by weight, in some embodiments less than about 5% by weight, and in some embodiments, less than about 1% by weight.

When dried, the relative percentages and solids add-on level of the resulting activated carbon coating may vary to achieve the desired level of odor control. The "solids add-on level" is determined by subtracting the weight of the untreated substrate from the weight of the treated substrate (after drying), dividing this calculated weight by the weight of the untreated substrate, and then multiplying by 100%. One particular benefit of the present invention is that high solids add-on levels and activated carbon levels are achievable without a substantial sacrifice in durability of the coating. In some embodiments, for example, the add-on level of the activated carbon ink is at least about 2%, in some embodiments from about 4% to about 40%, and in some embodiments, from about 6% to about 35%. Further, the coating may contain from about 10 wt. % to about 80 wt. %, in some embodiments from about 20 wt. % from about 70 wt. %, and in some embodiments, from about 40 wt. % to about 60 wt. % of activated carbon. Likewise, the coating may also contain from about 10 wt. % to about 80 wt. %, in some embodiments from about 10 wt. % from about 60 wt. %, and in some embodiments, from about 30 wt. % to about 50 wt. % of binder.

D. Additional Inks

To further improve the aesthetic appeal of the odor control substrate, one or more additional inks may also be employed that contrast with the color of the activated carbon ink (e.g., black). Possible colors that contrast well with a black ink include, for instance, white, yellow, cyan, magenta, red, green, blue, etc. However, any ink may generally be employed so long as some perceivable difference exists between the colors of the inks. To provide the desired color, the colored ink may include a colorant, such as a pigment, dye, etc. The colorant may constitute from about 0.01 to about 20 wt. %, in some embodiments from about 0.1 wt. % to about 10 wt. %, and in some embodiments, from about 0.5 wt. % to about 5 wt. % of the colored ink. For example, the colorant may be an inorganic and/or organic pigment. Some examples of commercially available organic pigments that may be used in the present invention include those that are available from Clariant Corp. of Charlotte, N.C., under the trade designations GRAPHTOL® or CARTAREN®. Other pigments, such as lake compounds (blue lake, red lake, yellow lake, etc.), may also be employed. Inorganic and/or organic dyes may also be utilized as a colorant. Exemplary organic dye classes include triarylmethyl dyes, monoazo dyes, thiazine dyes, oxazine dyes, naphthalimide dyes, azine dyes, cyanine dyes, indigo dyes, coumarin dyes, benzimidazole dyes, paraquinoidal dyes, fluorescein dyes, diazonium salt dyes, azoic diazo dyes, phenylenediamine dyes, diazo dyes, anthraquinone dyes, trisazo dyes, xanthene dyes, proflavine dyes, sulfonaphthalein dyes, phthalocyanine dyes, carotenoid dyes, carminic acid dyes, azure dyes, acridine dyes, and so forth. One particularly suitable class of dyes includes anthraquinone compounds, which may be classified for identification by their Color Index (CI) number. For instance, some suitable anthraquinones that may be used in the present invention, as classified by their "CI" number, include Acid Black 48, Acid Blue 25 (D&C Green No. 5), Acid Blue 40, Acid Blue 41, Acid Blue 45, Acid Blue 129, Acid Green 25, Acid Green 27, Acid Green 41, Mordant Red 11 (Alizarin), Mordant Black 13 (Alizarin Blue Black B), Mordant Red 3 (Alizarin Red S), Mordant Violet 5 (Alizarin Violet 3R), Natural Red 4 (Carminic Acid), Disperse Blue 1, Disperse Blue 3, Disperse Blue 14, Natural Red 16 (Purpurin), Natural Red 8, Reactive Blue 2, and so forth.

Besides a colorant, the ink may also include various other components as is well known in the art, such as colorant stabilizers, photoinitiators, binders, solvents, surfactants, humectants, biocides or biostats, electrolytic salts, pH adjusters, etc.

For example, various components for use in an ink are described in U.S. Pat. Nos. 5,681,380 to Nohr, et al. and U.S.

Pat. No. 6,524,379 to Nohr, et al., which are incorporated herein in their entirety by reference thereto for all purposes. Such inks typically contain water as a principal solvent, and particularly deionized water in an amount from about 20 wt. % to about 95 wt. % of the ink. Various co-solvents may also be included in the ink formulation. Examples of such co-solvents include a lactam, such as N-methyl pyrrolidone. Other examples of optional co-solvents include N-methylacetamide, N-methylmorpholine-N-oxide, N,N-dimethylacetamide, N-methyl formamide, propyleneglycol-monomethyl-ether, tetramethylene sulfone, and tripropyleneglycolmonomethylether. Still other co-solvents that may be used include propylene glycol and triethanolamine (TEA). If an acetamide-based co-solvent is included in the formulation, it is typically present within a range of from about 1 to about 12 wt. %.

Humectants may also be utilized, such as in an amount between about 0.5 and 20 wt. % of the ink. Examples of such humectants include, but are not limited to, ethylene glycol; diethylene glycol; glycerine; polyethylene glycol 200, 400, and 600; propane 1,3 diol; propylene-glycolmonomethyl ethers, such as Dowanol PM (Gallade Chemical Inc., Santa Ana, Calif.); polyhydric alcohols; or combinations thereof. Other additives may also be included to improve ink performance, such as a chelating agent to sequester metal ions that could become involved in chemical reactions over time, a corrosion inhibitor to help protect metal components of the printer or ink delivery system, a biocide or biostat to control unwanted bacterial, fungal, or yeast growth in the ink, and a surfactant to adjust the ink surface tension. If a surfactant is included, it is typically present in an amount of between about 0.1 to about 1.0 wt. %. If a corrosion inhibitor is included, it is typically present in an amount between about 0.1 and about 1.0 wt. %. If a biocide or biostat is included, it is typically present in an amount between about 0.1 and about 0.5 wt. %.

The colored inks may be formed by any known process. For instance, one such process involves mixing all of the components together, heating the mixture to a temperature of from about 40° C. to about 55° C. for a period of from about 2 to about 3 hours, cooling the mixture to room temperature (typically from about 10° C. to about 35° C.), and filtering the mixture to obtain an ink. The viscosity of the resulting ink is typically is no more than about 5 centipoise, and in some embodiments from about 1 to about 2.5 centipoise.

The process for forming a patterned substrate having an activated carbon ink and an additional ink may involve sequentially applying the inks onto one or more surfaces of the substrate. The colored ink may be applied to the same surface as the activated carbon ink so that a readily visible pattern is achieved. Alternatively, the activated carbon ink and colored ink may be applied on opposing surfaces so that the colored ink acts as a contrasting background for the activated carbon ink. The colored ink may generally be applied using any known method, such as those referred to above. The colored ink may be uniformly applied to the substrate surface, or applied in a pattern that covers less than 100% of the area of the surface.

Figure 1B:
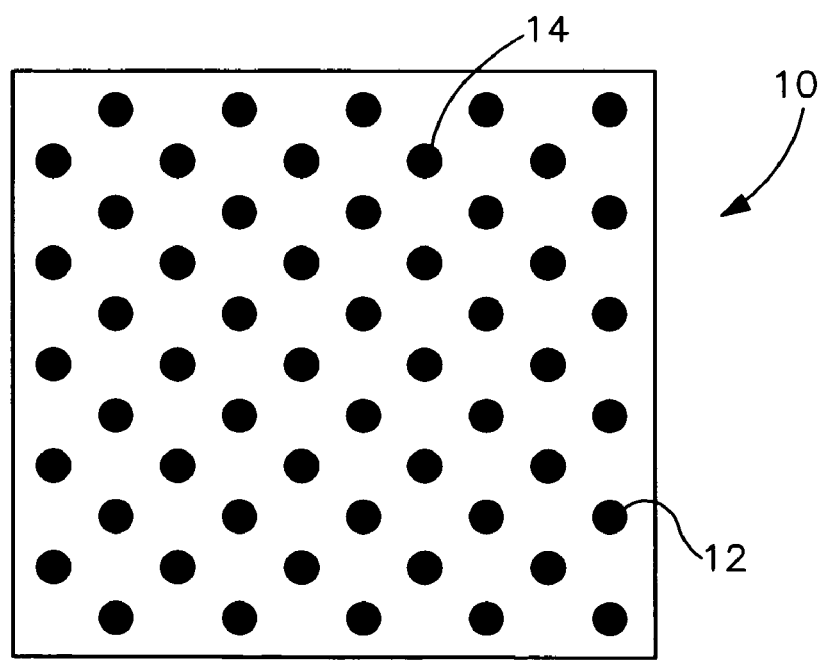
FIG. 1B depicts an activated carbon ink printed on top of a colored ink.

When utilized, the colored and activated carbon inks may be applied in an overlapping or non-overlapping relationship. Referring to FIG. 1A, for instance, one embodiment of a patterned substrate 10 is shown in which an ink 12 is printed on top of an activated carbon ink 14 in an overlapping relationship. FIG. 1B illustrates an alternative embodiment in which the activated carbon ink 14 is printed on top of the ink 12. In either case, the top ink generally does not cover the entire surface area of the bottom ink. This is to ensure that the activated carbon ink is able to contact and adsorb odorous compounds, and that a clear pattern is observed. For example, the top ink may cover less than about 90%, in some embodiments less than about 75%, and in some embodiments, less than about 50% of the surface area of the bottom ink.

Figure 2:
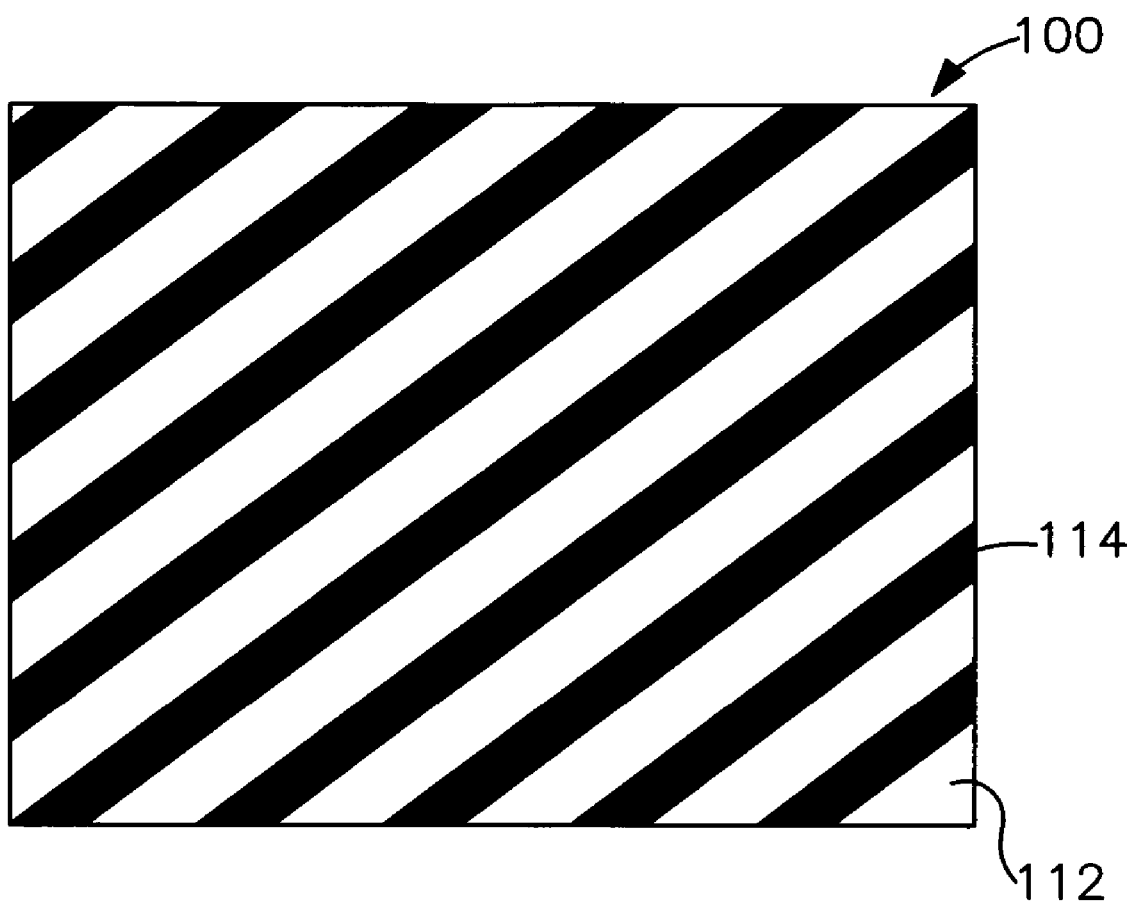
FIG. 2 illustrates an odor control substrate having non-overlapping color patterns in accordance with another embodiment of the present invention.

On the other hand, referring to FIG. 2, another substrate 100 is shown that includes an ink 112 and an activated carbon ink 114 applied in a non-overlapping relationship. Such a non-overlapping relationship may provide a variety of benefits to the resulting odor control substrate 100. For example, in certain cases, the activated carbon ink 114 might have an adverse affect on the flexibility, absorbency, and/or some other characteristic of the substrate 100. By minimizing the area to which the activated carbon ink 114 is applied, any such adverse affect is minimized. In addition, a non-overlapping relationship may also provide a clearer definition of the pattern provided by the inks.

E. Articles

Figure 3:
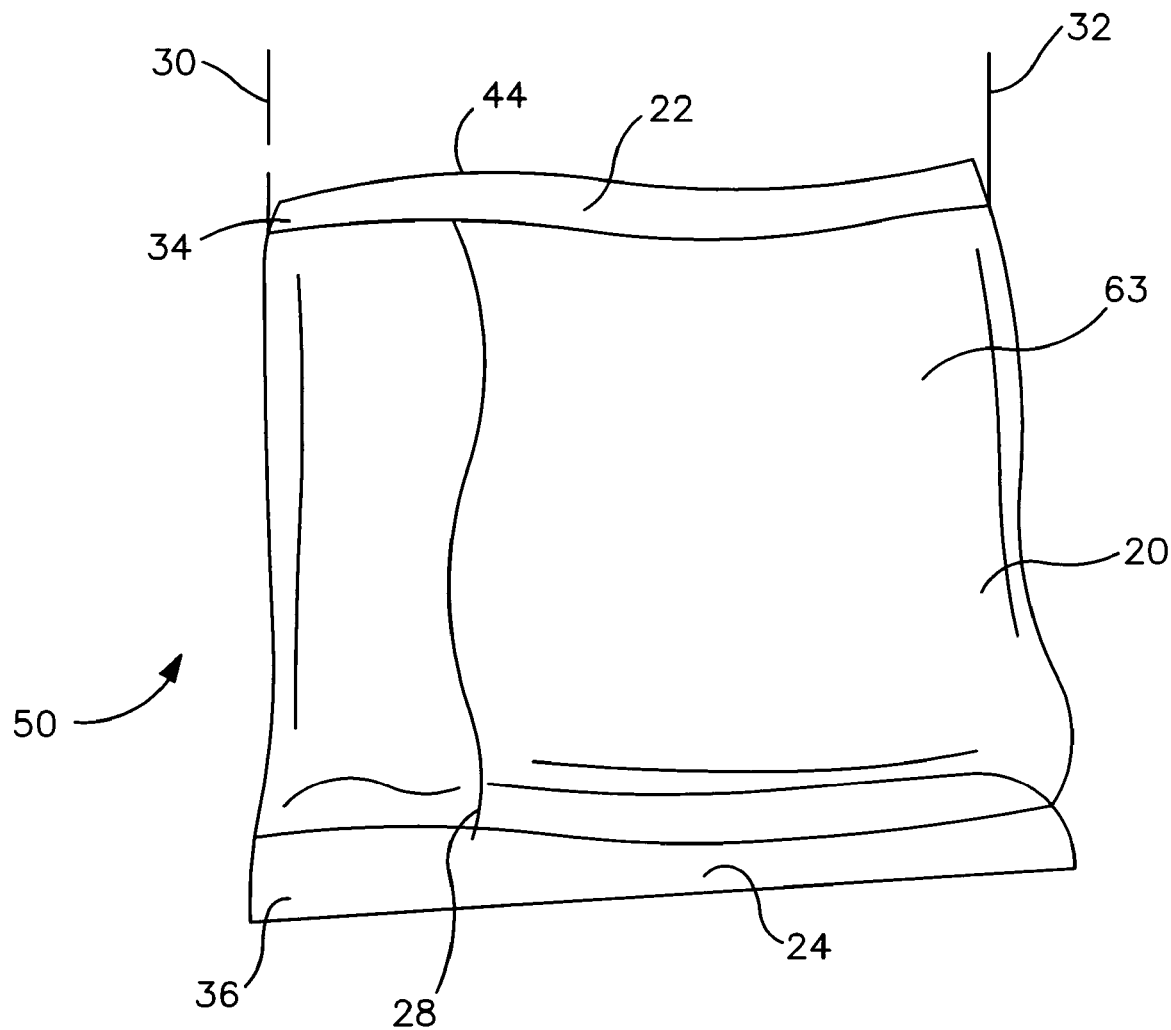
FIG. 3 is a perspective view of one embodiment of an individually wrapped absorbent article package of the present invention.
Figure 4:
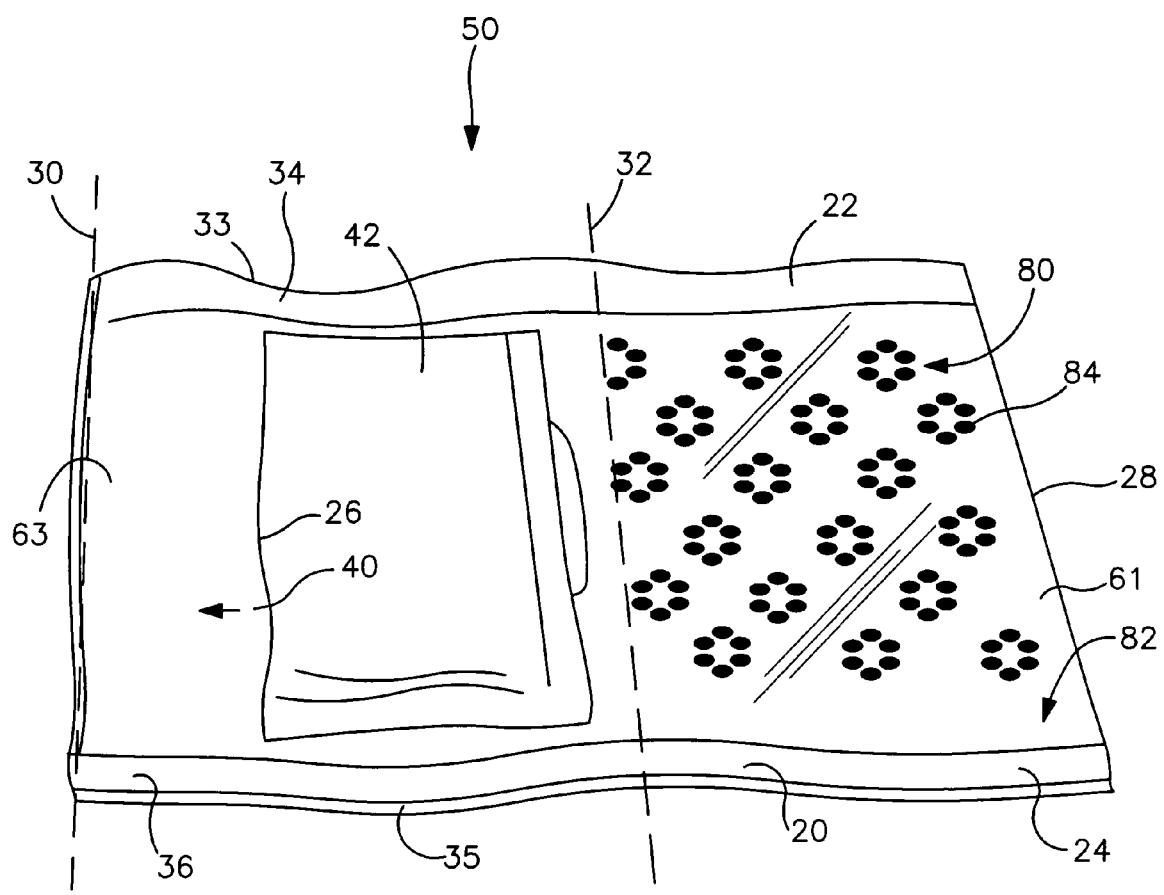
FIG. 4 is a perspective view of the package of FIG. 1 shown in its opened state.

The patterned odor control substrate of the present invention may be employed in a wide range of articles. In one particular embodiment, the patterned odor control substrate is used to form a pouch for an absorbent article. Specifically, many absorbent articles (e.g., feminine hygiene products) are disposed by placing them in a small pouch in which the product is packaged for sale. Thus, the odor control substrate of the present invention may be employed in the pouch to help reduce odors associated with the dispensed absorbent articles. Referring to FIGS. 3-4, for example, one embodiment of an individually wrapped absorbent article package 50 is illustrated. As shown, an absorbent article 42 is carried in the package 50, which for purposes of description only, is shown as a feminine care product (e.g., sanitary pad or napkin). The absorbent article 42 may be folded in any desired pattern to fit in the package 50.

The package 50 includes an elongate piece of wrapper 44 that is folded and bonded into the desired pouch configuration. For example, the wrapper 44 may be an elongated rectangular piece having a first end 26, an opposite second end 28, and generally parallel longitudinal sides 33 and 35 extending between the ends 26 and 28. Various other pouch configurations are known and used in the art for individually packaging feminine care absorbent articles and any such configuration may be used in a package according to the invention.

For example, various other pouch configurations are disclosed in U.S. Pat. Nos. 6,716,203 to Sorebo, et al. and U.S. Pat. No. 6,380,455 to Moder, et al., as well as U.S. Patent Application Publication No. 2003/0116462 to Sorebo, et al., all of which are incorporated herein in their entirety by reference thereto for all purposes. In the illustrated embodiment, for example, a pouch 40 is shown that is similar to the pouch configuration used for Kotex® Ultrathin pads available from Kimberly-Clark Corporation.

The wrapper 44 is essentially folded around the absorbent article 42 such that the pouch 40 is formed around the article. The wrapper 44 is first folded at a first fold axis 30 such that the first end 26 is folded towards but spaced from the second end 28. The distance between the first end 26 and second end 28 may vary depending on the desired length of a resulting flap 20, as described below. The aligned longitudinal sides of the wrapper 44 define sides 34 and 36 of the pouch 40. The second end 28 of the wrapper 44 is then folded at a second fold axis 32 so as to extend back over the first end 26 and thus defines the flap 20 that closes off the pouch 40. The flap 20 has longitudinal sides 24 and 22 that align with the material sides 33 and 35 and pouch sides 34 and 36. The sides of the pouch 40 are then bonded in a conventional manner, for example with a heat/pressure embossing roll. The flap sides 22 and 24 are bonded to the material sides 33 and 35 and pouch sides 34 and 36 in a single pass operation. It may be the case that the first end 26 of the wrapper 44 extends essentially to the second fold axis 32 and, thus, the flap sides 22 and 24 would be bonded along their entire length to pouch sides 34 and 36. The edge of the second end 28 may extend across the front surface of the pouch 40. It may be desired to adhere all or a portion of this edge to the pouch surface. However, in a desirable embodiment, this edge is left un-adhered to the pouch between its bonded sides 22 and 24.

Regardless of the particular pouch configuration, the wrapper 44 may be formed from a variety of different materials, including a film, a fibrous material (e.g., nonwoven web), and combinations thereof. For example, the wrapper 44 may sometimes contain a breathable film. In one particular embodiment, the odor control substrate of the present invention is used to form one or materials of the wrapper 44. Typically, when utilized in this manner, it is desired that the pattern of inks is visible to the user and also capable of adsorbing odorous compounds. For example, as shown, a pattern 80 of an activated carbon ink 84 is applied over a colored ink 82. In this particular embodiment, the inks 82 and 84 are present on an inner surface 61 of the wrapper 44 so that they are more readily able to contact odorous compounds stemming from the absorbent article 42. Alternatively, however, the inks 82 and/or 84 may also be present on other surfaces of the wrapper 44, such as an outer surface 63.

Besides being used in a pouch configuration, the substrate may also be used in one or more components of an absorbent article, such as in a liquid-permeable layer (e.g., bodyside liner, surge layer, etc.), liquid-impermeable or breathable layer (e.g., outer cover, ventilation layer, baffle, etc.), absorbent core, elastic member, and so forth. Several examples of such absorbent articles are described in U.S. Pat. No. 5,197,959 to Buell; U.S. Pat. No. 5,085,654 to Buell; U.S. Pat. No. 5,634,916 to Lavon, et al.; U.S. Pat. No. 5,569,234 to Buell, et al.; U.S. Pat. No. 5,716,349 to Taylor, et al.; U.S. Pat. No. 4,950,264 to Osborn, III; U.S. Pat. No. 5,009,653 to Osborn, III; U.S. Pat. No. 5,509,914 to Osborn, III; U.S. Pat. No. 5,649,916 to DiPalma, et al.; U.S. Pat. No. 5,267,992 to Van Tillburg; U.S. Pat. No. 4,687,478 to Van Tillburg; U.S. Pat. No. 4,285,343 to McNair; U.S. Pat. No. 4,608,047 to Mattingly; U.S. Pat. No. 5,342,342 to Kitaoka; U.S. Pat. No. 5,190,563 to Herron, et al.; U.S. Pat. No. 5,702,378 to Widlund, et al.; U.S. Pat. No. 5,308,346 to Sneller, et al.; U.S. Pat. No. 6,110,158 to Kielpikowski; U.S. Pat. No. 6,663,611 to Blaney, et al.; and WO 99/00093 to Patterson, et al., which are incorporated herein in their entirety by reference thereto for all purposes.

The odor control substrate of the present invention is versatile and may also be used with other types of articles of manufacture. For instance, the odor control substrate may be used in air filters, such as house filters, vent filters, disposable facemasks, and facemask filters. Exemplary facemasks, for instance, are described and shown, for example, in U.S. Pat. Nos. 4,802,473; 4,969,457; 5,322,061; 5,383,450; 5,553,608; 5,020,533; 5,813,398; and 6,427,693, which are incorporated herein in their entirety by reference thereto for all purposes. In one embodiment, the odor control substrate of the present invention may be utilized as a filtration layer of the facemask. Filtration layers, such as meltblown nonwoven webs, spunbond nonwoven webs, and laminates thereof, are well known in the art.

In still other embodiments, the odor control substrate may be employed in conjunction with a garment. For instance, garments, such as meat and seafood packing industry aprons/attire, grocery store aprons, paper mill aprons/attire, farm/dairy garments, hunting garments, etc., may be incorporated with the odor control substrate of the present invention. As an example, hunters often wear garments that are camouflaged for the particular hunting environment. The odor control substrate of the present invention may thus be used to form the patterned camouflage pattern. Specifically, the odor control substrate may impart the desired color pattern and also help reduce human odor during hunting. In addition, the odor control coating may be employed on a cover for pet beds, chairs, elder care/hospital bed covers, infant/children cribs, and so forth.

The effectiveness of the odor control substrate of the present invention in reducing odor may be measured in a variety of ways. For example, the percent of an odorous compound adsorbed by the odor control substrate may be determined using the headspace gas chromatography test as set forth herein. In some embodiments, for instance, the odor control substrate of the present invention is capable of adsorbing at least about 25%, in some embodiments at least about 45%, and in some embodiments, at least about 65% of a particular odorous compound. The effectiveness of the activated carbon ink in removing odors may also be measured in terms of "Relative Adsorption Efficiency", which is also determined using headspace gas chromatography and measured in terms of milligrams of odor adsorbed per gram of the activated carbon ink. It should be recognized that the surface chemistry of any one type of activated carbon ink may not be suitable to reduce all types of odors, and that low adsorption of one or more odorous compounds may be compensated by good adsorption of other odorous compounds.

The present invention may be better understood with reference to the following examples.

Test Methods

Quantitative odor adsorption was determined in the Examples using a test known as "Headspace Gas Chromatography." Headspace gas chromatography testing was conducted on an Agilent Technologies 5890, Series II gas chromatograph with an Agilent Technology 7694 headspace sampler (Agilent Technologies, Waldbronn, Germany). Helium was used as the carrier gas (injection port pressure: 12.7 psig; headspace vial pressure: 15.8 psig; supply line pressure is at 60 psig). A DB-624 column was used for the odorous compound that had a length of 30 meters and an internal diameter of 0.25 millimeters. Such a column is available from J&W Scientific, Inc. of Folsom, Calif.

The operating parameters used for the headspace gas chromatography are shown below in Table 1:

TABLE 1

| Operating Parameters for the Headspace Gas Chromatography Device. Headspace Parameters | | |
|---|---|---|
| Zone Temps, ° C. | Oven | 37 |
| | Loop | 85 |
| | TR. Line | 90 |
| Event Time, minutes | GC Cycle time | 10.0 |
| | Vial eq. Time | 10.0 |
| | Pressuriz. Time | 0.20 |
| | Loop fill time | 0.20 |
| | Loop eq. Time | 0.15 |
| | Inject time | 0.30 |
| Vial Parameters | First vial | 1 |
| | Last vial | 1 |
| | Shake | [off] |

The test procedure involved placing 0.005 to 0.1 grams of a sample in a 20 cubic centimeter (cc) headspace vial. Using a syringe, an aliquot of an odorous compound was also placed in the vial. Specifically, testing was done with 2.0 micrograms of ethyl mercaptan (2.4 microliters) and 1.8 micrograms (2 microliters) of dimethyldisulfide. The samples were tested in triplicate. After ten minutes, a hollow needle was inserted through the septum and into the vial. A 1-cubic centimeter sample of the headspace (air inside the vial) was then injected into the gas chromatograph. Initially, a control vial with only the aliquot of odorous compound was tested to define 0% odorous compound adsorption. To calculate the amount of headspace odorous compound removed by the sample, the peak area for the odorous compound from the vial with the sample was compared to the peak area from the odorous compound control vial.

EXAMPLE 1

The ability to apply activated carbon ink to a substrate was demonstrated. The activated carbon ink was made by Mead-Westvaco Corp. under the name "Nuchar PMA", and contained 15 wt. % activated carbon, 12 wt. % styrene-acrylic copolymer binder, and 73 wt. % water. Flat steel rolls were used in a standard off-set gravure printing system (obtained from Faustel Inc. of Germantown, Wis.) to uniformly print the activated carbon ink onto one side of the polyethylene film. The film had a basis weight of 27.1 grams per square meter, and had been previously exposed to a corona discharge treatment as is well known in the art. After printing, the films were dried with a through-air dryer at a temperature of 190° F. for approximately 5 seconds. Seven (7) different samples were printed with the activated carbon ink in the above-described manner, each having varying coating weights and print patterns. The line speeds and coating weights (also calculated as solids add-on level) used for the activated carbon samples are set forth below in Table 2.

TABLE 2

Activated Carbon Samples

| Sample | Line Speed for Printing (ft/min) | Coating Weight (gsm) | Solids Add-On Level (%) |
|---|---|---|---|
| Control | — | — | — |
| 1 | 100 | 8.5 | 31.4 |
| 2 | 100 | 2.8 | 10.3 |
| 3 | 100 | 2.8 | 10.3 |
| 4 | 100 | 3.5 | 12.9 |
| 5 | 100 | 0.6 | 2.2 |
| 6 | 1000 | 4.3 | 15.9 |
| 7 | 1000 | 4.3 | 15.9 |

Several of the samples were then tested for their ability to remove ethyl mercaptan and dimethylsulfide odorous compounds using the headspace gas chromatography test described above. The results are set forth below in Table 3.

TABLE 3

Odor Reduction

| Sample | Ethyl Mercaptan (% removed) | Dimethyldisulfide (% removed) |
|---|---|---|
| 1 | 66.0 | 61.5 |
| 2 | 45.0 | 71.8 |
| 4 | 56.0 | 71.4 |
| 5 | 35.9 | 55.9 |

Figure 5:
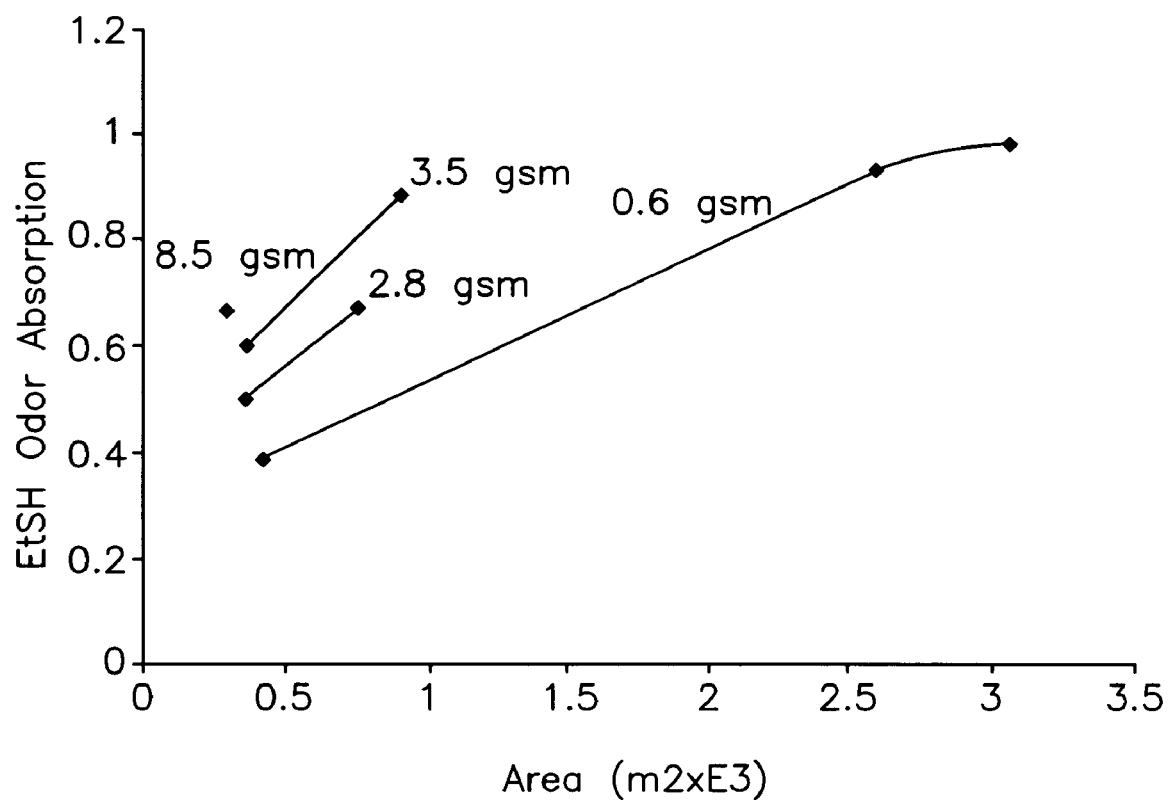
FIG. 5 graphically depicts the results of the Example 1, in which the odor adsorption of ethyl mercaptan is plotted versus coverage area for various coating weights.

The above odor reduction data was then employed to obtain a correlation between coating weight and the percent coverage (i.e., print pattern). The study measured the odor adsorption capacity for different sample areas having the same coating weight. In other words, different sample sizes were cut out from the same coated film, and the odor capacity was then measured. This was repeated for all the films having different coating weights. Referring to FIG. 5, a graph is depicted of the resulting odor adsorption isotherms for each coating. From this graph, one may determine the coating weight (or solids add-on level) required for a desired print area and odor capacity. Alternatively, one may also determine the print area required for a desired coating weight (or solids add-on level) and odor capacity.

EXAMPLE 2

The ability to apply activated carbon ink to a substrate in a certain pattern was demonstrated. The activated carbon ink was made by MeadWestvaco Corp. under the name "Nuchar PMA", and contained 15 wt. % activated carbon, 12 wt. % styrene-acrylic copolymer binder, and 73 wt. % water. Gravure steel rolls were used in a standard off-set gravure printing system (obtained from Faustel Inc. of Germantown, Wis.) to print the activated carbon ink onto one side of the polyethylene film. The film had a basis weight of 27.1 grams per square meter, and had been previously exposed to a corona discharge treatment as is well known in the art. After printing, the films were dried with a through-air dryer at a temperature of 190° F. for approximately 5 seconds.

The activated carbon ink was printed in a floral pattern on the film at various coating weights (or solids add-on levels) and patterns. Several of the samples were then tested for their ability to remove ethyl mercaptan odorous compounds using the headspace gas chromatography device described above. The results are set forth below in Table 4.

TABLE 4

Activated Carbon Samples

| Sample | Line Speed (ft/min) | Coating Weight (gsm) | Solids Add-On Level (%) | Surface Area Covered (%) | Ethyl Mercaptan (% removed) |
|---|---|---|---|---|---|
| 8 | 100 | 6 | 22.1 | 25 | 20 |
| 9 | 100 | 6 | 22.1 | 75 | 58 |
| 10 | 100 | 4 | 14.8 | 25 | 16 |
| 11 | 100 | 4 | 14.8 | 75 | 50 |

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for forming an odor control substrate, said method comprising:
   printing a first ink in a pattern onto a surface of said substrate, the ink comprising activated carbon particles and a polymer latex having a glass transition temperature of about 30° C. or less, wherein said first ink is discontinuous over the surface so that the pattern covers from about 25% to about 95% of the area of said surface, and wherein said first ink presents a color that is visually distinguishable from another color presented by said substrate; and drying said first ink so that the solids add-on level is at least about 2%.

2. The method of claim 1, wherein said substrate contains a nonwoven web, a film, or combination thereof.

3. The method of claim 1, wherein said first ink covers from about 30% to about 90% of the area of said surface.

4. The method of claim 1, wherein the solids add-on level of said first ink is from about 4% to about 40%.

5. The method of claim 1, wherein the contrast between the color of said first ink and another color presented by the substrate has a minimum gray scale value of at least about 45 on a scale of 0-255.

6. The method of claim 1, wherein the color of said first ink is black.

7. The method of claim 1, further comprising printing a second ink onto said substrate that presents a color that is visually distinguishable from the color of said first ink.

8. The method of claim 7, wherein the color of said second ink is white, yellow, cyan, magenta, red, green, blue, or a combination thereof.

9. The method of claim 7, wherein said first and second inks are applied in an overlapping relationship.

10. The method of claim 7, wherein said first and second inks are applied in a non-overlapping relationship.

11. The method of claim 1, wherein said odor control substrate contains a liquid impermeable film.

12. The method of claim 1, wherein said odor control substrate contains a nonwoven web.

13. The method of claim 1, wherein said first ink further comprises masking particles.

14. The method of claim 1, wherein the pattern is in the form of indicia, floral designs, stripes, bands, dots, or a combination thereof.

15. The method of claim 1, wherein said first ink comprises from about 5 wt.% to about 25 wt. % of activated carbon particles.

16. The method of claim 1, wherein said first ink comprises from about 10 wt.% to about 20 wt. % of activated carbon particles.

17. The method of claim 1, wherein said first ink comprises from about 0.1 wt.% to about 20 wt. % of polymer latex.

18. The method of claim 1, wherein said first ink comprises from about 1 wt.% to about 15 wt. % of polymer latex.

19. The method of claim 1, wherein said first ink comprises water.

20. The method of claim 19, wherein said first ink comprises from about 60 wt. % to about 90 wt. % of water.

21. The method of claim 1, wherein said dried first ink comprises from about 40 wt. % to about 60 wt. % of activated carbon particles.

22. The method of claim 1, wherein said dried first ink comprises from about 30 wt. % to about 50 wt. % of polymer latex.

23. The method of claim 1, wherein the polymer latex has a glass transition temperature from about −15° C. to about 15° C.

24. The method of claim 1, wherein the polymer latex is a styrene polymer.

25. The method of claim 24, wherein the styrene polymer is a styrene acrylic copolymer.

26. The method of claim 11, wherein the film is breathable.

27. The method of claim 11, wherein the film has been exposed to a corona discharge treatment prior to printing the ink thereon.

28. The method of claim 11, further comprising folding the film into a pouch for individually wrapping an absorbent article wherein the surface of the film printed with the first ink comprises the inner surface of the pouch.

* * * * *